US008286088B2

(12) United States Patent  
Shaffer et al.

(10) Patent No.: US 8,286,088 B2  
(45) Date of Patent: *Oct. 9, 2012

(54) PATIENT MEDICAL PARAMETER TREND INDICATIVE USER INTERFACE DISPLAY SYSTEM

(75) Inventors: Judith Shaffer, Orchard Park, NY (US); Mark Penny, Salem, MA (US); Rand J. Monteleone, Acton, MA (US); Amy M. Manetta, North Billerica, MA (US); Jolyn Rutledge, Amesbury, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 2736 days.

This patent is subject to a terminal disclaimer.

(21) Appl. No.: 10/411,950

(22) Filed: Apr. 11, 2003

(65) Prior Publication Data

US 2004/0002874 A1    Jan. 1, 2004

Related U.S. Application Data

(60) Provisional application No. 60/374,908, filed on Apr. 23, 2002, provisional application No. 60/413,301, filed on Sep. 25, 2002.

(51) Int. Cl.
*G06F 3/048* (2006.01)
*G06F 17/21* (2006.01)
*G06F 17/00* (2006.01)
*G06Q 10/00* (2012.01)
*G08B 23/00* (2006.01)

(52) U.S. Cl. .............. 715/764; 705/2; 705/3; 340/573.1

(58) Field of Classification Search .................. 717/109; 705/9, 3, 2; 715/764; 340/573.1
See application file for complete search history.

(56) References Cited

U.S. PATENT DOCUMENTS 4,878,175 A   10/1989 Norden-Paul et al. ... 364/413.01
(Continued)

FOREIGN PATENT DOCUMENTS

WO       WO 02/32036 A2    4/2002

OTHER PUBLICATIONS

New Flowsheet Solution From McKesson Improves Nurse Efficiency, Enhances Medication Safety; Oct. 23, 2002. Horizon Expert Documentation Sets New Standard for "Smart" Workflow Technology Business/Medical Editors. Business Wire; New York.*

(Continued)

*Primary Examiner* — Jordany Nunez
(74) *Attorney, Agent, or Firm* — Jack Schwartz and Associates, PLLC (57) ABSTRACT

A system according to invention principles advantageously automatically displays a parameter value within the closest Flowsheet parameter acquisition time interval column. A user interface system provides patient medical parameter data for trend indicative display covering a time period comprising user selectable acquisition time intervals. The system includes an acquisition processor for acquiring, from a patient monitoring device, data representing a patient parameter comprising a plurality of data values at a corresponding plurality of different times within multiple user selectable patient parameter acquisition intervals of a time period. The data processor determines for a particular user selectable acquisition time interval a patient parameter data value closest in time to a center time point of the particular user selected acquisition time interval and excludes other patient parameter data values acquired within the particular user selectable acquisition time interval. A generator generates data representing an image showing a trend indicative display of the patient parameter including the determined patient parameter data value associated with the particular user selectable acquisition time interval and omits the excluded data values.

15 Claims, 13 Drawing Sheets

U.S. PATENT DOCUMENTS

| | | | | |
|---|---|---|---|---|
| 5,072,383 | A | 12/1991 | Brimm et al. | 364/413.02 |
| 5,077,666 | A | 12/1991 | Brimm et al. | 364/413.02 |
| 5,247,611 | A | 9/1993 | Norden-Paul et al. | 395/161 |
| 5,253,362 | A | 10/1993 | Nolan et al. | 395/600 |
| 5,301,319 | A | 4/1994 | Thurman et al. | 395/600 |
| 5,325,478 | A | 6/1994 | Shelton et al. | 395/148 |
| 5,468,222 | A | 11/1995 | Altchuler | 604/49 |
| 5,546,580 | A | 8/1996 | Seliger et al. | 305/600 |
| 5,592,945 | A | 1/1997 | Fiedler | 128/710 |
| 5,682,526 | A | 10/1997 | Smokoff et al. | 395/615 |
| 5,697,959 | A * | 12/1997 | Poore | 607/32 |
| 5,715,451 | A * | 2/1998 | Marlin | 707/104.1 |
| 5,812,983 | A | 9/1998 | Kumagai | 705/3 |
| 5,942,986 | A | 8/1999 | Shabot et al. | 340/825.44 |
| 5,950,168 | A * | 9/1999 | Simborg et al. | 705/3 |
| 6,081,809 | A | 6/2000 | Kumagai | 707/104 |
| 6,179,784 | B1 | 1/2001 | Daniels et al. | 600/538 |
| 6,311,162 | B1 | 10/2001 | Reichwein et al. | 705/1 |
| RE41,500 | E * | 8/2010 | Shelton et al. | 715/217 |
| 7,848,935 | B2 * | 12/2010 | Gotlib et al. | 705/2 |
| 2001/0050610 | A1 * | 12/2001 | Gelston | 340/5.53 |
| 2002/0044059 | A1 * | 4/2002 | Reeder et al. | 340/573.1 |
| 2002/0120676 | A1 | 8/2002 | Biondi et al. | 709/203 |
| 2002/0138512 | A1 | 9/2002 | Buresh et al. | 707/507 |
| 2003/0050794 | A1 | 3/2003 | Keck | 705/2 |
| 2004/0039628 | A1 * | 2/2004 | Thompson et al. | 705/9 |
| 2004/0186746 | A1 * | 9/2004 | Angst et al. | 705/3 |
| 2006/0080140 | A1 * | 4/2006 | Buttner et al. | 705/2 |
| 2011/0202370 | A1 * | 8/2011 | Green et al. | 705/3 |
| 2011/0246226 | A1 * | 10/2011 | Green et al. | 705/2 |

OTHER PUBLICATIONS

Anders Kaliner "Uncertainty in measurement; Introduction and examples from laboratory medicine" The Journal of the International Federation of Clinical Chemistry, 'Online! vol. 13, No. 1, Jan. 13, 2001, XP002296952.

* cited by examiner

PATIENT MEDICAL PARAMETER TREND INDICATIVE USER INTERFACE DISPLAY SYSTEM

This is a non-provisional application of provisional application Ser. No. 60/374,908 by A. M. Manetta et al. filed Apr. 23, 2002 and of provisional application Ser. No. 60/413,301 by J. Rutledge et al. filed Sep. 25, 2002. This application is related to application Ser. No. 10/359,673 filed Feb. 6, 2003 entitled A System and User Interface Supporting Trend Indicative Display of Patient Medical Parameters by A. M. Manetta et al.

FIELD OF THE INVENTION

This invention is related to adaptively processing and displaying of medical information, and more particularly to processing and displaying patient medical data for user configurable display in a network environment.

BACKGROUND OF THE INVENTION

Patient medical parameter data is acquired, collated, stored and displayed for use in providing patient clinical care in hospitals, clinics, and other healthcare delivery settings. Patient medical parameter data may include vital signs ventilator information, infusion pump data associated with fluid delivery and other data. Such patient medical parameter data is typically displayed on a patient monitoring device screen in a trend indicative chart with a time axis. This type of chart is commonly termed a Flowsheet. A patient monitoring device is usually located at a patient bedside or nursing station in a hospital ward or in an intensive care, surgical or other location and may be connected to a network such as the Internet, a LAN, a WAN or an intra-net for acquiring patient parameter data from local sources (e.g., patient attached sensors) or remote sources (e.g., a remotely stored electronic patient record). The Flowsheet is an electronic chronological chart of patient information that substitutes for a paper vital sign Flowsheet. It is desirable that an electronic Flowsheet offer similar or better features and flexibility than a paper Flowsheet chart that it replaces An electronic Flowsheet provides a trend indicative display covering a time period comprising user selectable patient parameter acquisition time intervals. A user selectable acquisition time interval is represented by a column in the Flowsheet and covers a time period (typically 3 minutes to 4 hours or another user selectable time interval) in which patient parameters are acquired. A problem occurs in known Flowsheet systems in selecting a parameter value to represent a particular parameter acquistion time interval in a trend indicative display. Specifically, in known systems a parameter value displayed in a particular acquistion time interval may not be representative of the time interval. This happens in known systems that label the acquisition time intervals with a displayed time value and automatically allocate a parameter value, received at a specific time, to a displayed labeled interval that precedes or includes the labeled time value. Similarly, it happens in known systems that automatically allocate a parameter value, received at a specific time, to a displayed labeled interval that follows or includes the labeled time value. Using these known systems, a displayed labeled interval may display a parameter value that is closer to an adjacent time interval and consequently present a misleading trend indicative display to a user. In such a known system, a manually entered parameter value or a parameter value indicated as accurate by a user may similarly be misleadingly displayed in an incorrect labeled time interval. A system according to invention principles addresses these problems and derivative problems.

SUMMARY OF THE INVENTION

A system according to invention principles advantageously automatically displays a parameter closest in time to a centre time point of a particular Flowsheet parameter acquisition time interval column. A system provides patient medical parameter data for trend indicative display covering a time period comprising user selectable acquisition time intervals. The system includes an acquisition processor for, receiving user entered data identifying an acquisition time interval duration and acquiring data representing a patient parameter comprising a plurality of data values at a corresponding plurality of different times within multiple patient parameter acquisition time intervals individually having the duration. A data processor for determining, for the multiple patient parameter acquisition time intervals of the duration, patient parameter data values closest in time to substantial centre time points of the multiple patient parameter acquisition time intervals and for excluding other patient parameter data values acquired within the multiple patient parameter acquisition time intervals.

DETAILED DESCRIPTION

The inventors have recognized that it is desirable to provide a digital Flowsheet that automatically displays a selected parameter value in a particular Flowsheet time interval column closest in time to a centre time point of the particular Flowsheet column. For this purpose, the system advantageously stores and examines parameters acquired within half an acquisition time interval either side of the centre time point of the particular Flowsheet column. The system selects from the examined parameter values, a parameter value for display in the particular Flowsheet column that is measured at a time closest to the centre time point of the particular Flowsheet column. However, a manually entered parameter value for a particular Flowsheet acquisition time interval is taken as representative of the Flowsheet acquisition interval and is not replaced by an automatically received parameter value. This is so even if the automatically received value is closer to a Flowsheet acquisition interval centre time. A user entered parameter value, indicated as validated in response to user command via a displayed image, is not replaced by automatically acquired patient parameter data.

Figure 1:
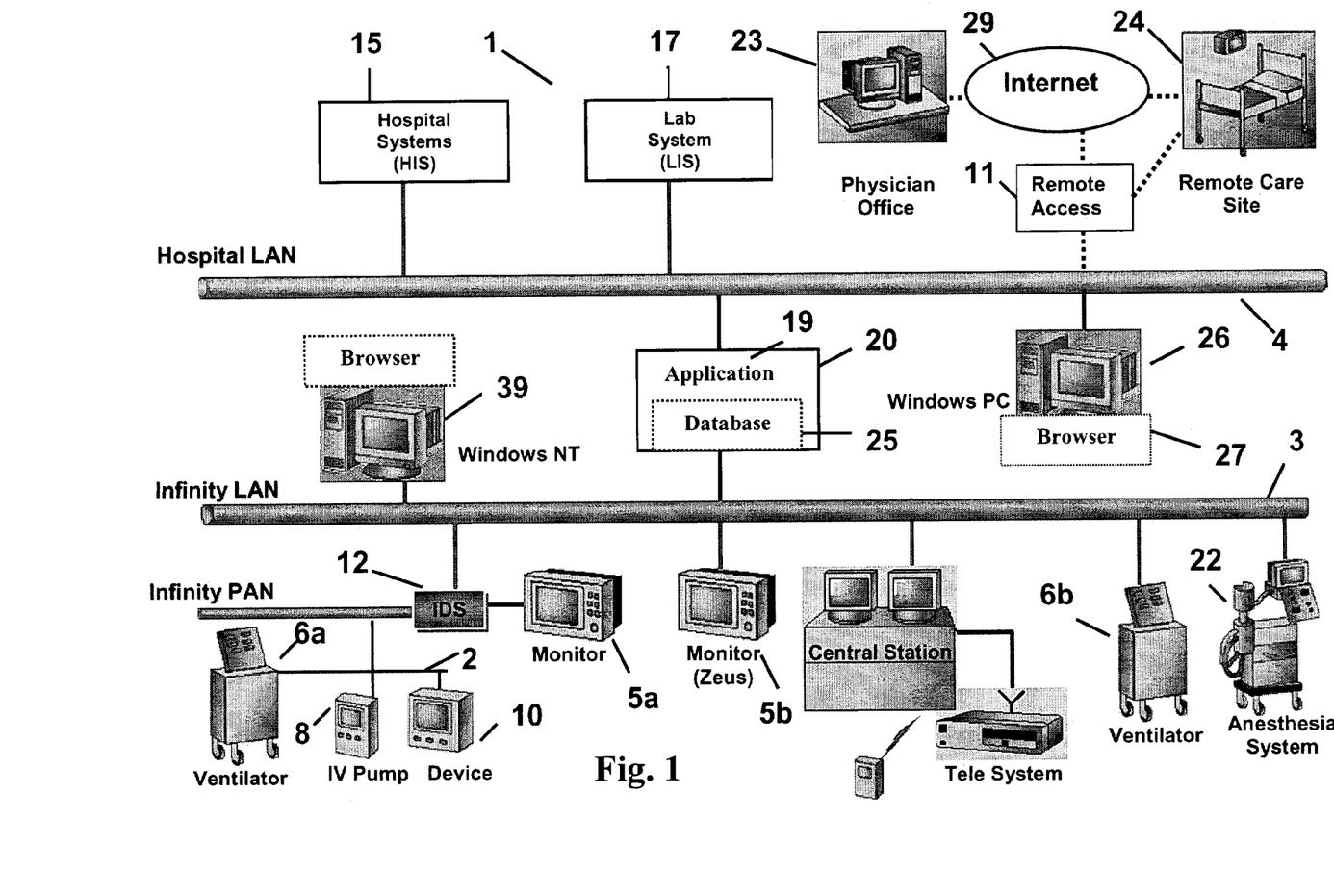
FIG. 1 is a block diagram of a communication network with various devices, according to the principles of the invention.

FIG. 1 is an exemplary block diagram of a communication network incorporating server 20 hosting executable application 19 providing a trend indicative user interface display of patient parameters (termed a Flowsheet) within identified acquisition time intervals. A Flowsheet may display different types of parameters associated with, for example, Intra-Venous fluids, drip administered medications, blood products, blood pressure, ventilation, laboratory test data, tissue scores, vital signs, blood oxygen concentration, and infusion pump fluid delivery. In an alternative embodiment, the executable application providing the Flowsheet user interface may be resident in another processing device in any part of the network shown in FIG. 1. Communication network 1 (FIG. 1) is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown In FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a care unit such as a patient's room within a nursing station to administer care to a particular patient and to monitor the particular patient. Various medical devices may be connected via MIB 2; examples shown in FIG. 1 comprise a ventilator 6a, IV (Intravenous) Pump 8 or other medical equipment 10. MIB 2 is typically connected to a second level LAN network 3 through an Interface Docking Station (IDS) device 12, for interfacing to Ethernet-compatible LAN network 3. The LAN 3 may be for example, an Infinity LAN, marketed by Siemens Medical System. This higher-level LAN 3 is typically, though not necessarily, used by other care units such as a particular department within a hospital, such as an intensive care unit or surgery unit, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a ventilator 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 11 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 11 may also be part of server 20, to be described below, instead of standing alone, as well know in the art.

According to the principles of the present invention, executable application 19 (or multiple applications in another embodiment) resides on central server 20 on LAN 3 for gathering and processing data from the peripheral medical devices or facilities coupled to LAN 3 or hospital LAN 4, including laboratory results supplied via laboratory system 17 connected through an HL7 interface, for example. Additional medical parameter data including additional laboratory results acquired from any number of medical devices such as those shown in FIG. 1 may be obtained by server 20 using ASTM messaging, for example. The acquired medical parameters associated with a given patient, including laboratory test results, are acquired from the medical devices on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. An example of server 20, is a Prometheus server, marketed by Siemens Medical System. The server may be hosted, for example, by a computer system that is capable of running Microsoft NT operating system.

Patient parameter data acquired from patient attached equipment may be characterized as of continuous or discrete type. Continuous patient parameter data is periodically sampled and acquired at intervals typically of higher frequency than a displayed acquisition interval and discrete patient parameter data is acquired at non-periodic intervals (e.g., upon nurse measurement initiation) or at periodic intervals of relatively low frequency compared to continuous patient parameter data. Application 19 automatically advantageously filters acquired continuous patient parameter data by selecting a patient parameter value that substantially occurs at (or is reasonably near) the centre time of an individual acquisition time interval for display in a Flowsheet column representing an acquisition time interval. Specifically, the selected continuous patient parameter value is incorporated in an Internet compatible (web based) Flowsheet column representing the individual acquisition time interval. Application 19 automatically advantageously filters discrete acquired patient parameter data by selecting a patient parameter value that occurs at a time closest to the centre time of an individual acquisition time interval for display in a Flowsheet column. Further, application 19 supports generation of a Cursor Tool and user interface image windows enabling a clinician (or other user) to examine, edit, validate or annotate filtered data points or to select alternative acquired patient parameter data points to represent Flowsheet column acquisition intervals (and to override automatically filtered data).

Application 19 provides a user interface trend indicative display of patient parameters (a Flowsheet) covering a time period comprising user selectable acquisition time intervals. A user selectable acquisition time interval represented by a column in the Flowsheet covers a time period (typically 3 minutes to 4 hours or another user selectable range) in which patient parameters are acquired. Application 19 automatically filters acquired patient parameter data by selecting a patient parameter value for display in a Flowsheet column representing an individual acquisition time interval. Specifically, the selected patient parameter value is incorporated in an Internet compatible (web based) Flowsheet column representing the individual acquisition time interval.

Figure 2:
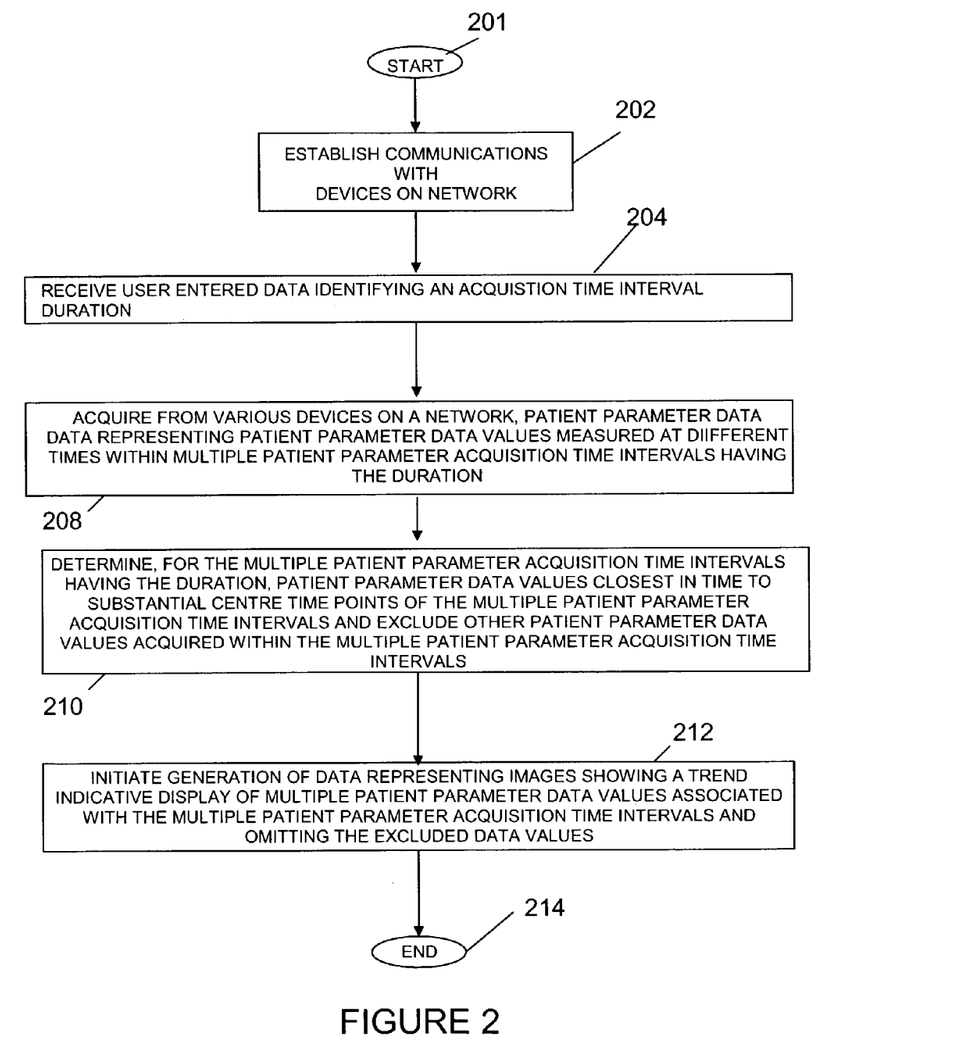
FIG. 2 represents a flowchart of a method for providing a user interface, according to the present invention.

FIG. 2 shows in flow chart form, functions that are performed by executable application 19. Application 19 establishes communication with devices on the network as shown in step 202 after the start at step 201. This is done, for example, by using IP protocol and the known IP device address for each device on the network 1 (FIG. 1), in conjunction with any higher application-layer protocols, as well known in the art. Once communication is established between server 20 and the other devices, application 19, in step 204, receives user entered data identifying an acquisition time interval duration. In step 208 application 19 acquires, from various devices on the network, data representing a patient parameter comprising multiple data values at corresponding multiple different times within multiple patient parameter acquisition time intervals individually having the duration. The parameter may comprise, a blood pressure parameter, a respiratory or ventilation parameter, a vital sign parameter, a blood oxygen concentration representative parameter, an infusion pump parameter associated with fluid delivery, a drip medication related parameter and another fluid related parameter, for example. Other parameters being acquired include laboratory results and settings selected for various monitoring devices. As previously mentioned, laboratory results may be obtained through an HL7 interface with LIS 17, or via ASTM or MIB point of care (POC) medical devices depicted in FIG. 1.

Medical data and laboratory results may be continuously, periodically or non-periodically acquired and correlated with a given patient for storage in relational data base 25 within server 20. Data base 25 may be of the type used for storing relational data such as the Microsoft SQL server. In addition, application 19 may obtain patient parameter data and patient data comprising medical laboratory results that are first entered and stored, for example, in laboratory system 17 of FIG. 1. Also, application 19 may acquire healthcare provider entered medical notes for display. In step 210 application 19 determines, for the multiple patient parameter acquisition time intervals of the user selected duration, patient parameter data values closest in time to substantial centre time points of the multiple patient parameter acquisition time intervals. Application 19 excludes other patient parameter data values acquired within the multiple patient parameter acquisition time intervals. Flowsheet columns representing the multiple patient parameter acquisition time intervals are identified and labeled in the Flowsheet image display with the determined centre time point values.

The patient parameter data values closest in time to the centre time points of the multiple patient parameter acquisition time intervals are determined by examining patient parameters acquired within substantially half an acquisition time interval either side of a centre time point. For a one hour interval a period of 30 minutes before and after the display column centre time point is examined. An acquisition time interval data value entered (or an existing data value marked) by a user, and thereby identified as being representative of a time interval, takes precedence over a data value determined to be closest in time to a centre time point of the time interval. Such a user entered or marked data value is not replaced by a data value selected based on closeness in time to a centre time point of the time interval. In response to user selection of a different acquisition time interval duration, application 19 repeats steps 204-210, and dynamically determines patient parameter data values closest in time to substantial centre time points of the multiple patient parameter acquisition time intervals of the new duration. Application 19 as previously described, excludes other patient parameter data values acquired within the multiple patient parameter acquisition time intervals of the new duration value.

Figure 3:
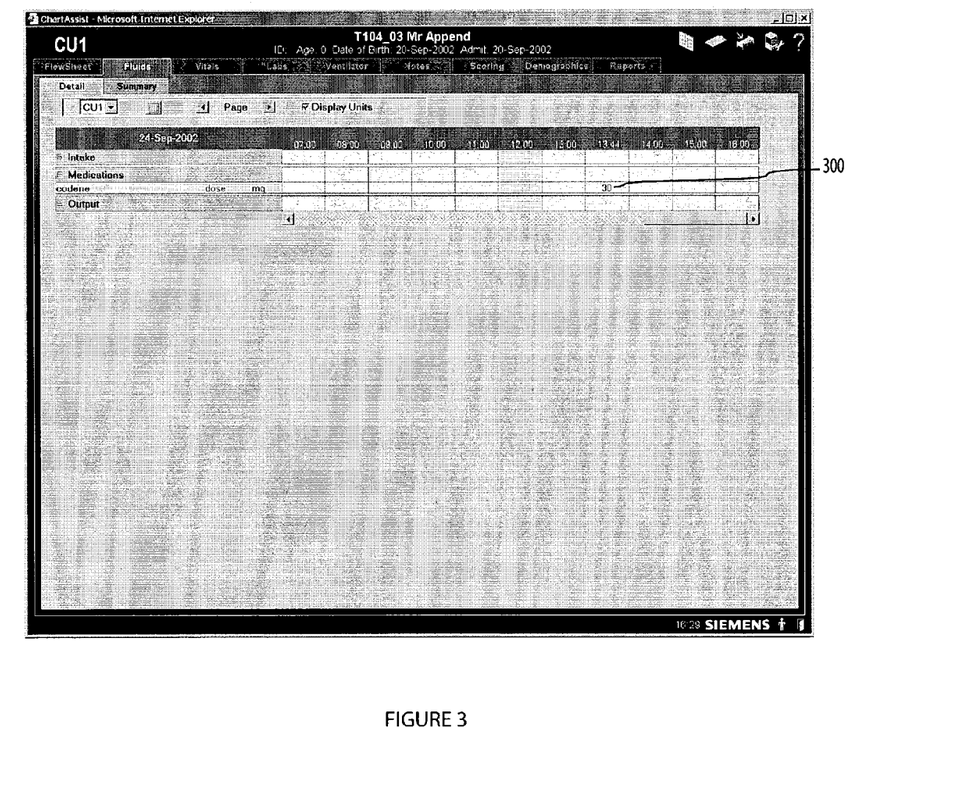
FIGS. 3-12 show user interface display images showing a Flowsheet trend indicative display of patient parameters, according to the present invention.
Figure 4:
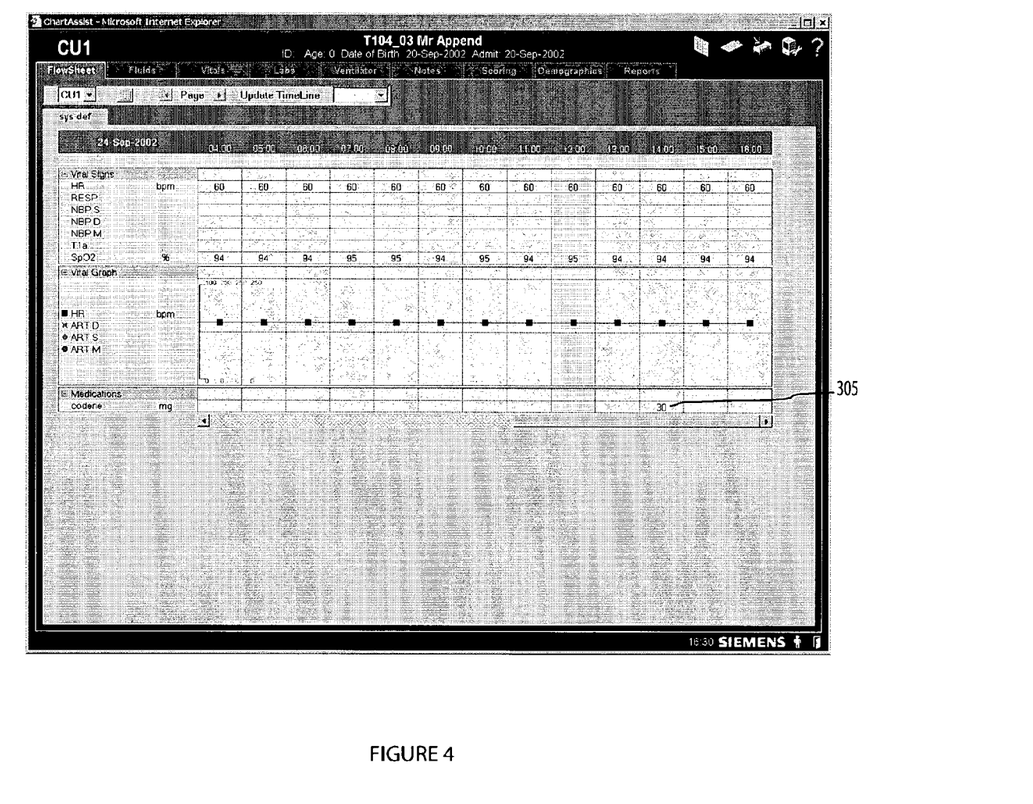

Application 19 in step 212 generates data representing an image showing Flowsheet trend indicative display of patient parameter data values associated with multiple patient parameter acquisition time intervals and omitting excluded data values. Specifically, application 19 initiates generation of an image exemplified by the images of FIGS. 3-12. In particular, images of FIGS. 3-7 illustrate operation of the system. The image of FIG. 3 shows a user entered Codeine medication of 30 units (item 300) administered at 13:44 pm being displayed in the Flowsheet trend indicative display of FIG. 4 during the parameter acquisition interval labeled 14:00 pm (item 305). This is because the Codeine medication is identified as being administered at 13:44 pm which is closest to the parameter acquisition interval labeled centre time of 14:00 pm.

Figure 5:
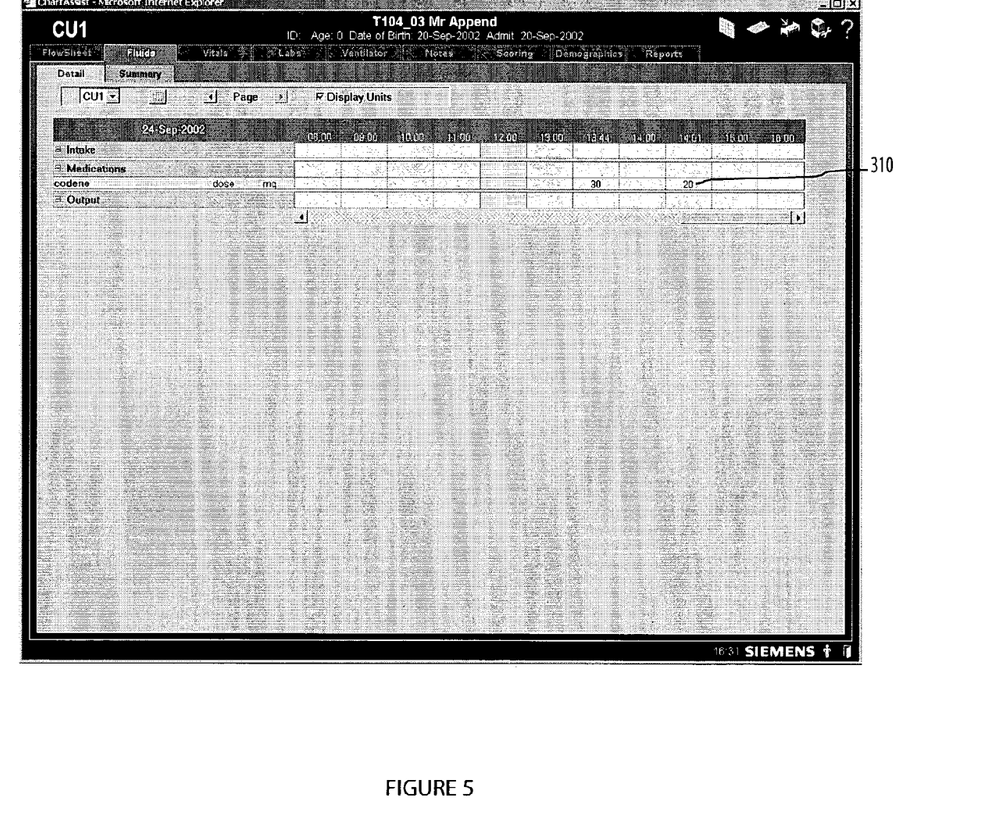
Figure 6:
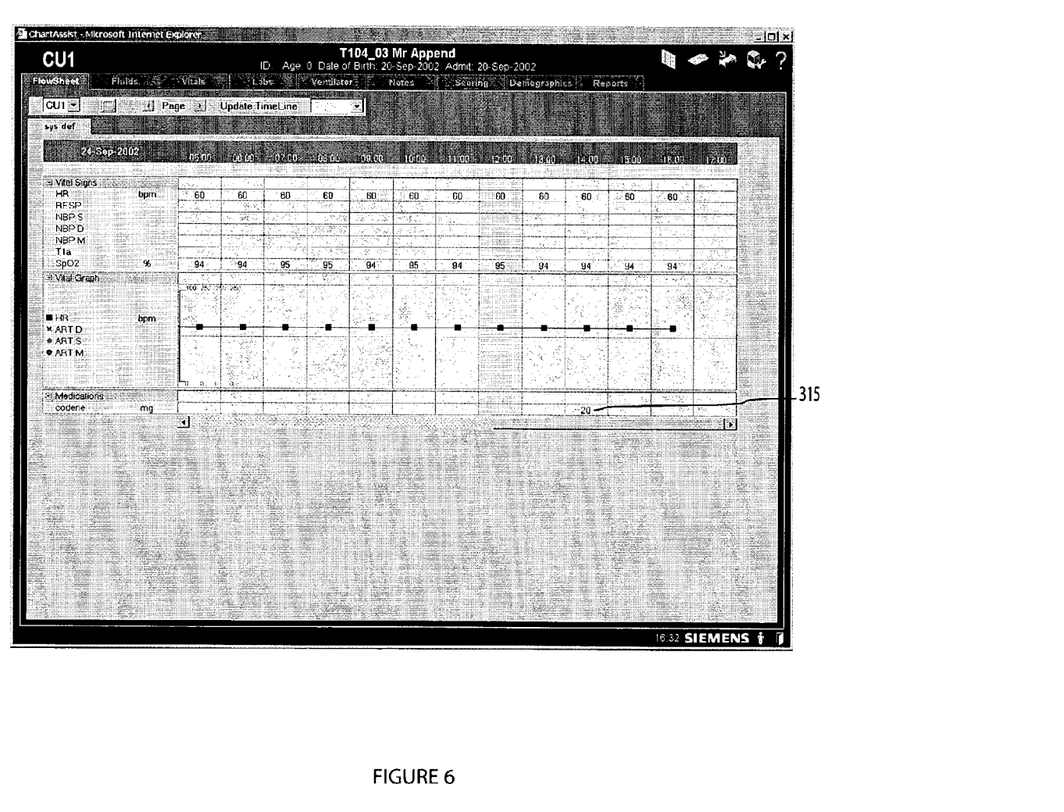
Figure 7:
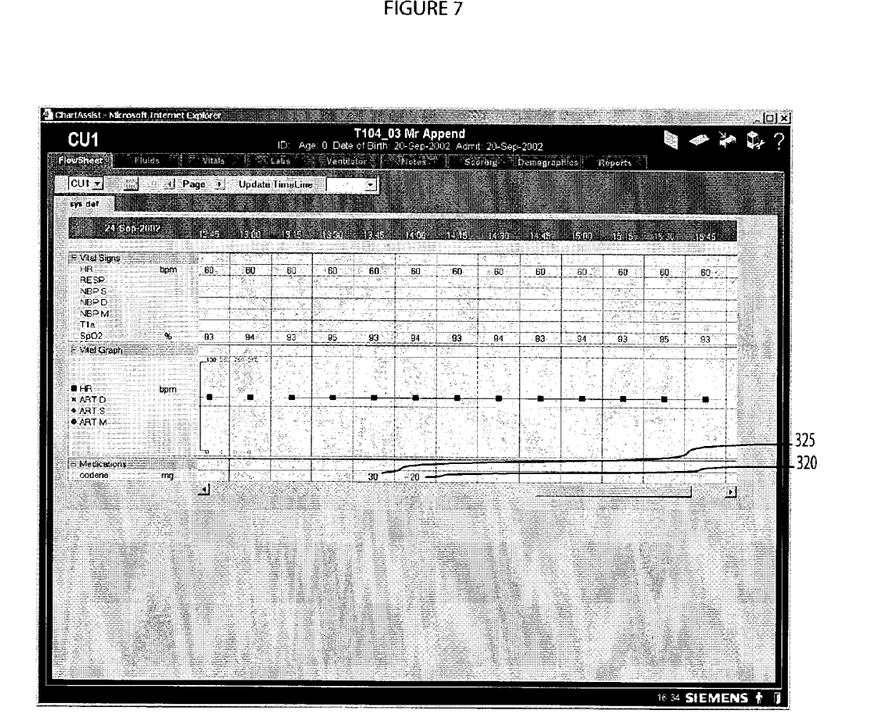

In response to a user entering another Codeine dose of 20 units for that same patient at 14:01 pm, as indicated as item 310 in the image of FIG. 5, the Flowsheet image acquisition interval labeled with centre time of 14:00 pm changes to show the entered 20 units (as shown as item 315 of FIG. 6). The 30 unit dose is excluded as the 20 unit dose is entered closer in time to the 14:00 pm interval centre time. If a user places a cursor over the displayed item 315 (e.g., using a mouse, or other cursor manipulation device), the user entered time associated with the 20 unit dose (14:01 pm) is advantageously displayed. In addition, in response to a user selecting a different parameter acquisition time interval of 15 minutes instead of one hour (as in FIGS. 3-6) both the 20 unit and 30 unit values are shown, as illustrated by items 320 and 325 respectively of FIG. 7. This is because the 30 unit dose entry time (13:44 pm) is closest to the interval labeled centre time of 13:45 pm and the 20 unit dose entry time (14:00 pm) is closest to the interval labeled centre time of 14:00 pm. Also, if a user indicates (by data entry) that the 20 unit dose value of 14:01 pm is to represent the time interval, even if another Codeine dose value closer to 14:00 pm is entered, the 20 unit dose takes precedence and is displayed as representing the 14:00 pm column time interval.

Figure 8:
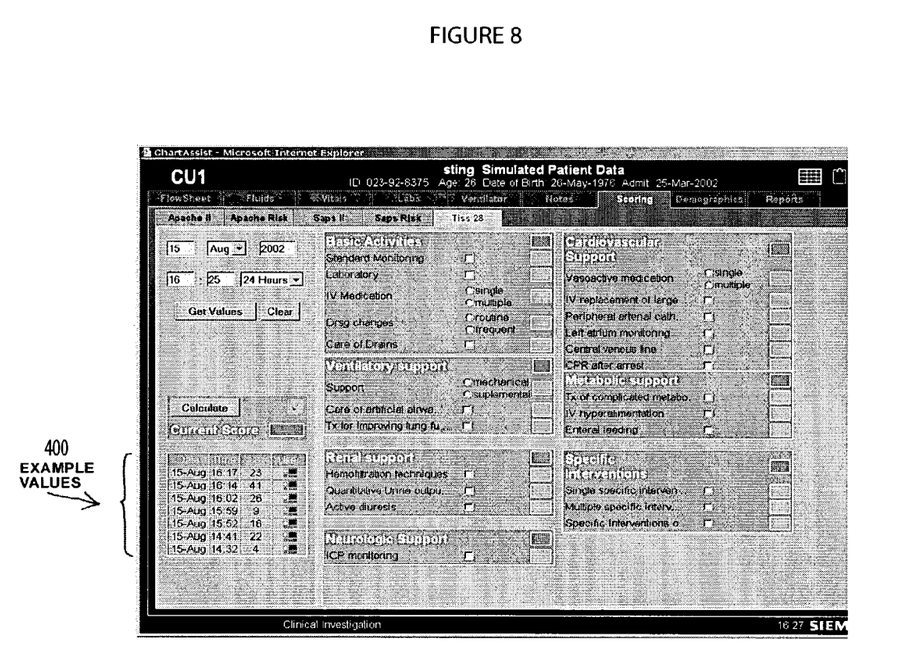
Figure 9:
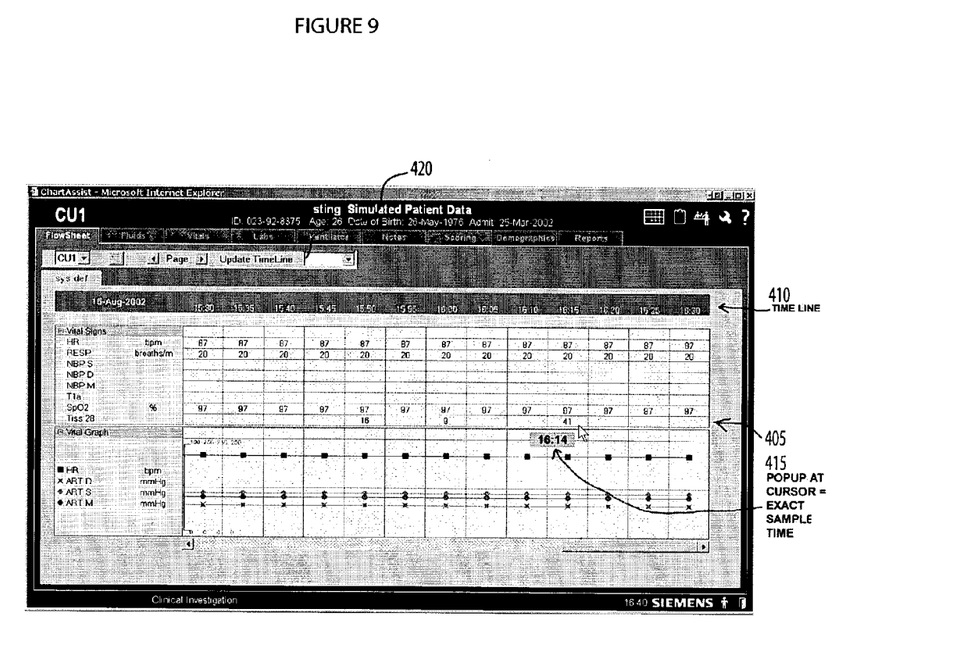
Figure 10:
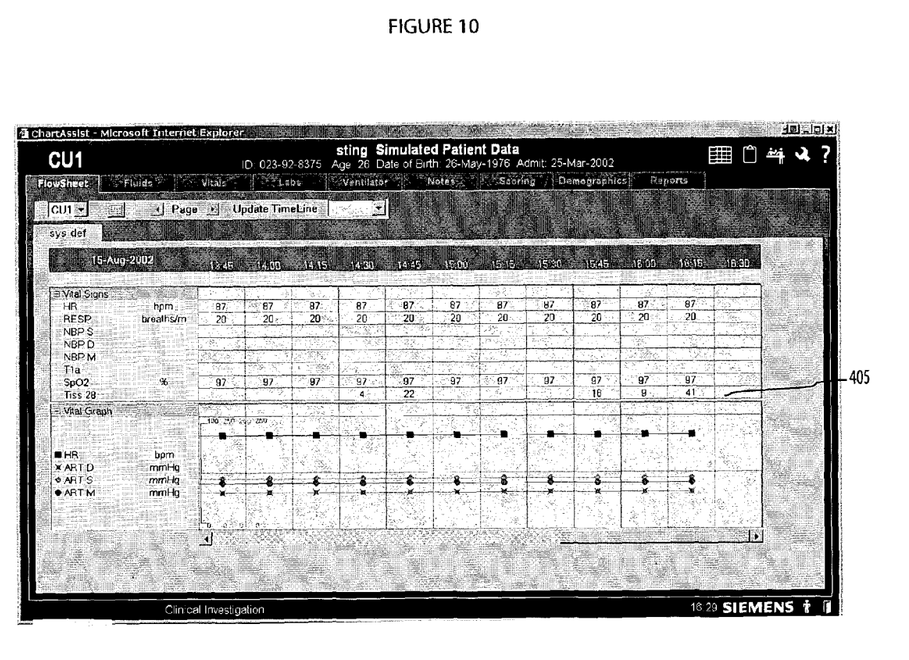
Figure 11:
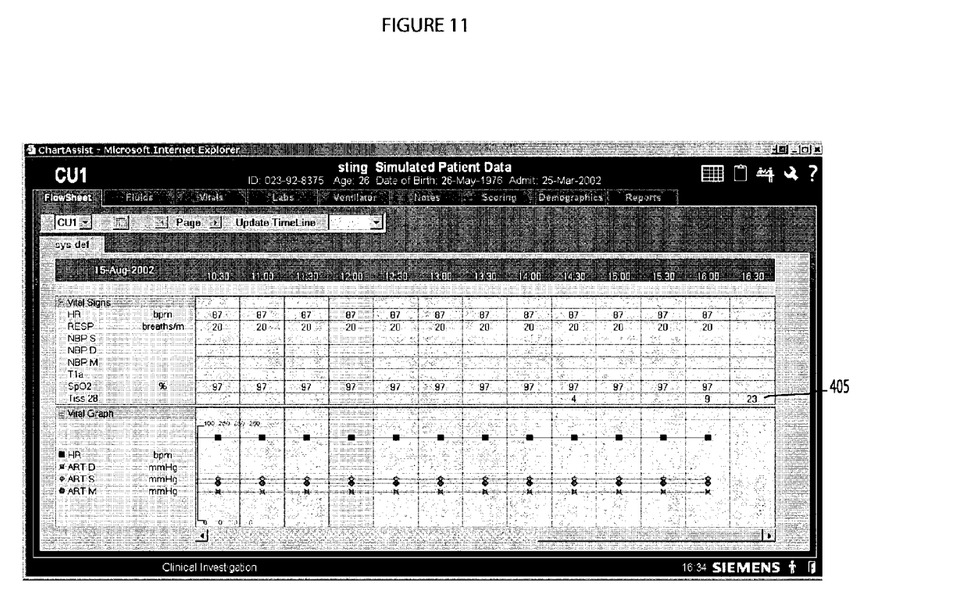
Figure 12:
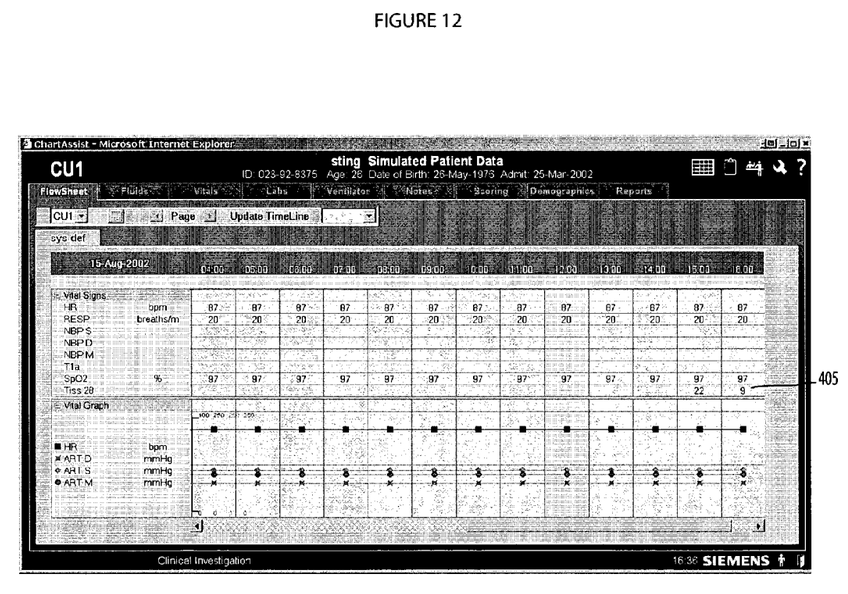

Display images of FIGS. 8-12 further illustrate system operation showing Flowsheet trend indicative display of the same data values 400 (TISS28 Scoring values) of FIG. 8 within parameter acquisition time intervals of different duration. The images of FIGS. 9-12 illustrate selection of particular values of TISS28 scoring data values 400 for Flowsheet display based on data value closeness to the labeled column centre time. The images of FIGS. 9-12 also show continuously acquired data values (e.g. HR-Heart Rate) associated with a column labeled centre time. FIG. 9 shows the exemplary tissue scoring data values in row 405 displayed in 5 minute duration acquisition time intervals between 15:30 and 16:30 pm as indicated in the time line 410. Row 405 shows three data values in columns with centre times of 15:50, 16:00 and 16:15. If a user places a cursor over the displayed value (41) in the 16:15 time interval column (e.g., using a mouse), the user entered time associated with value (16:14 pm, item 415) is displayed. Further, in response to user selection of a different (15 minute) time interval duration using update time line display element 420 of FIG. 9, the exemplary data values are displayed in FIG. 10 row 405 in 15 minute duration intervals. Five values are displayed in FIG. 10 in columns with centre times of 14:30, 14:45, 15:45, 16:00 and 16:15. Similarly, FIG. 11 shows three data values displayed in row 405 in columns with centre times of 14:30, 16:00 and 16:30 (30 minute duration intervals) and FIG. 12 shows two data values displayed in row 405 in columns with centre times of 15:00 and 16:00 (one hour duration intervals).

In one aspect of the present invention, a user may use a Microsoft Windows compatible PC 26 or Windows NT compatible PC 39 as shown in FIG. 1, or any other processing devices capable of running a menu generating program such as a web browser program (e.g., Microsoft Internet Explorer or Netscape Navigator, etc.) to view a Flowsheet, medical parameters and laboratory results information associated with a given patient. That is, a user may use a web browser on any processing device, as long as a communication connection can be made to server 20 and application 19, to make requests and view information acquired and stored in data base 25. This is advantageous, since a doctor may for example, gain access to a Flowsheet or laboratory test results from, for example, a remote physician's office 23, without having to access a dedicated terminal. Of course, a user can simply use a keyboard and/or a mouse or any other user interface devices to enter a user selection or request on a user computer, as is known in the art. Application 19 is therefore capable of collating and formatting medical data to be compatible with, for example, HTML (HyperText Mark-up Language) programming language for displaying data on a web browser. Application 19 is also responsive to, for example, HTTP (HyperText Transfer Protocol) commands originated from a user's web browser for making a request. The process of FIG. 2 ends at step 214.

Figure 13:
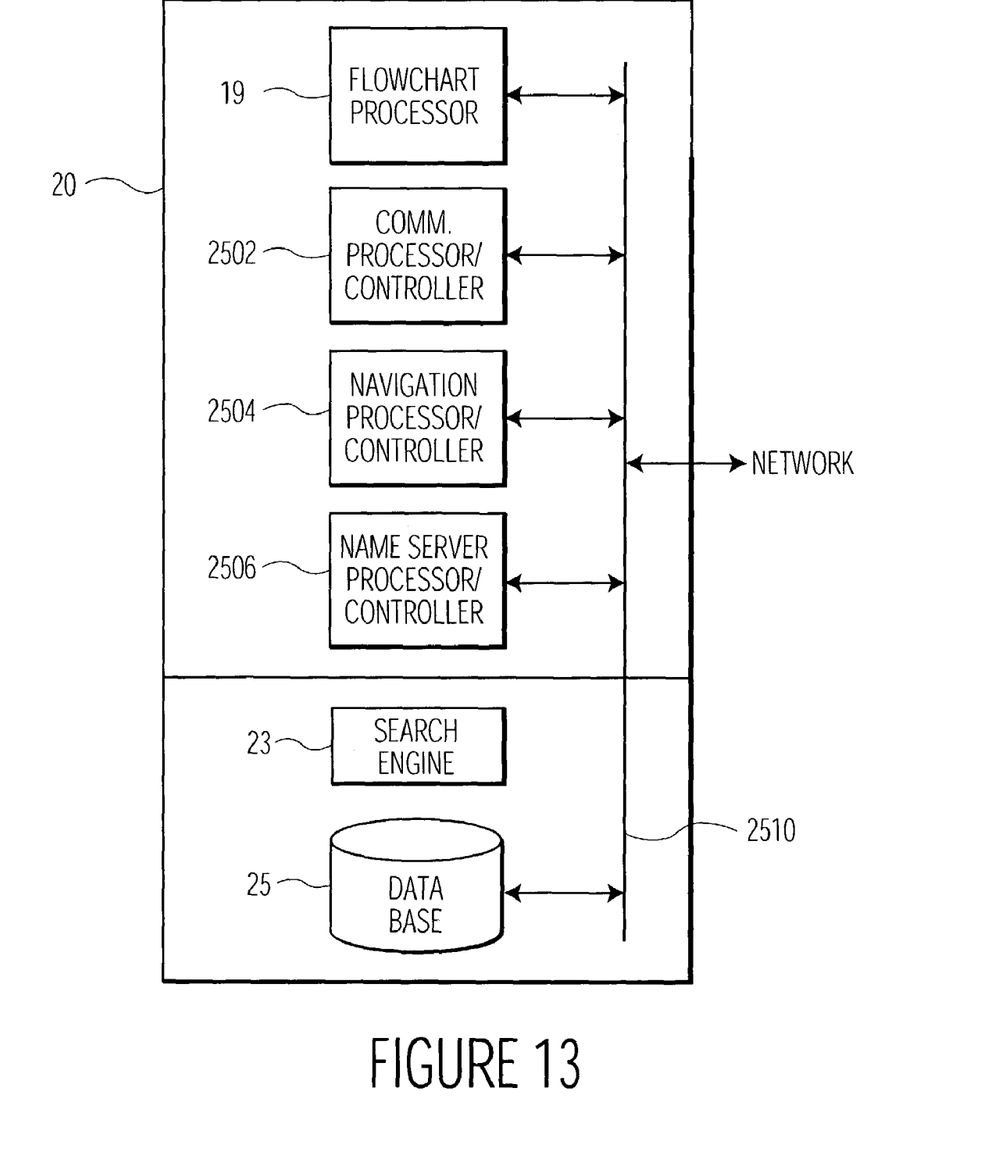
FIG. 13 is a block diagram of a server having functionality in accordance with the present invention.

FIG. 13 shows a block diagram of an exemplary embodiment of server 20 (FIG. 1) including functions in accordance with the present invention for generating data for configuring and presenting a Flowsheet trend indicative display and for managing, collating, searching and updating data base 25 containing patient medical information. Executable applications or processors operative to carry out instructions for performing the various functions described herein include an executable application 19 for performing Flowchart related processing and communications processing module 2502 that acquires the patient data including the monitored parameters allocated to a given patient from the network and collates the information for storage in data base 25. Navigation collation processor 2504 operates in conjunction with the web browser and display generator software to collate and prioritize parameters for display to the user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The Flowchart user interface display images, systems and processes presented in FIGS. 1-13 are not exclusive. Other Flowchart configuration and presentation display images, systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. The system advantageously enables a user to select continuous and discrete (episodic) data from a database for presentation in a user selected time period duration.

What is claimed is:

1. A system for providing patient medical parameter data for trend indicative display covering a time period comprising user selectable acquisition time intervals, comprising:
    an acquisition processor for,
        receiving user entered data identifying an acquisition time interval duration, and
        acquiring data representing a patient parameter using a patient monitoring device having at least one patient connected sensor, the data representing the patient parameter comprising a plurality of data values at a corresponding plurality of different times within multiple patient parameter acquisition time intervals individually having said duration; and
    a data processor for determining, for said multiple patient parameter acquisition time intervals having said duration, patient parameter data values closest in time to substantial centre time points of said multiple patient parameter acquisition time intervals and for excluding other patient parameter data values acquired within said multiple patient parameter acquisition time intervals.

2. A system according to claim 1, including
    a generator for generating data representing an image showing a trend indicative display of said plurality of patient parameter data values associated with said multiple patient parameter acquisition time intervals and omitting said excluded data values.

3. A system according to claim 1, wherein
    said acquisition processor receives user entered data identifying a second acquisition time interval duration, and
    said data processor dynamically determines, for multiple patient parameter acquisition time intervals of said second duration, patient parameter data values closest in time to substantial centre time points of said multiple patient parameter acquisition time intervals of said second duration and excludes other patient parameter data values acquired within said multiple patient parameter acquisition time intervals of said second duration.

4. A user interface system for providing patient medical parameter data for trend indicative display covering a time period comprising user selectable acquisition time intervals, comprising:
    an acquisition processor for acquiring data representing a patient parameter using a patient monitoring device having at least one patient connected sensor, the data representing the patient parameter comprising a plurality of data values at a corresponding plurality of different times within multiple user selectable patient parameter acquisition intervals comprising a time period;
    a data processor for determining for a particular user selectable acquisition time interval a patient parameter data value closest in time to a substantially centre time point of said particular user selected acquisition time interval and for excluding other patient parameter data values acquired within said particular user selectable acquisition time interval; and
    a generator for generating data representing an image showing a trend indicative display of said patient parameter including said determined patient parameter data value associated with said particular user selectable acquisition time interval and omitting said excluded data values.

5. A user interface system according to claim 4, wherein
    in response to user selection of a plurality of second acquisition time intervals comprising said time period and said second acquisition time interval is different to said particular user selectable acquisition time interval,
    said data processor automatically determines another patient parameter data value closest in time to a centre time point of said second acquisition time interval and excludes other patient parameter data values acquired within said second acquisition time interval.

6. A user interface system according to claim 4, wherein
    in response to user command and entry of a patient parameter data value,
    said data processor uses said user entered data value as said determined patient parameter data value associated with said particular user selectable acquisition time interval and excludes other patient parameter data values acquired within said particular user selectable acquisition time interval.

7. A user interface-system according to claim 6, wherein said data processor excludes a non-user entered patient parameter data value acquired within said particular user selectable acquisition time interval, said non-user entered patient parameter data value being closer in time to said centre time point of said particular user selected acquisition interval.

8. A user interface system according to claim 4, wherein said patient parameter comprises at least one of, (a) a blood pressure parameter, (b) a ventilation parameter, (c) a vital sign parameter, (d) a blood oxygen concentration representative parameter, (e) an infusion pump parameter associated with fluid delivery.

9. A user interface system according to claim 4, wherein said data processor determines said patient parameter data value closest in time to a centre time point of said particular user selected acquisition time interval by examining patient parameters acquired within substantially half an acquisition time interval either side of said centre time point.

10. A user interface system according to claim 4, wherein in response to a user positioning a cursor in the proximity of said patient parameter point in said image showing said trend indicative display, a time associated with at least one of, (a) measurement and (b) acquisition, of said patient parameter point is displayed.

11. A user interface system according to claim 4, wherein said acquisition processor acquires said data representing a patient parameter comprising said plurality of data values from a patient monitoring device.

12. A method for providing patient medical parameter data for trend indicative display covering a time period comprising user selectable acquisition time intervals, comprising the activities of:
  receiving user entered data identifying an acquisition time interval duration;
  acquiring, from a patient monitoring device using at least one patient connected sensor, data representing a patient parameter comprising a plurality of data values at a corresponding plurality of different times within multiple patient parameter acquisition time intervals individually having said duration;
  determining, for said multiple patient parameter acquisition time intervals having said duration, patient parameter data values closest in time to substantial centre time points of said multiple patient parameter acquisition time intervals; and
  excluding other patient parameter data values acquired within said multiple patient parameter acquisition time intervals.

13. A non-transitory storage medium according to claim 12, including computer readable instructions for implementing the activities of claim 12.

14. A method for providing patient medical parameter data for trend indicative display covering a time period comprising user selectable acquisition time intervals, comprising the activities of:
  acquiring, from a patient monitoring device, data representing a patient parameter comprising a plurality of data values at a corresponding plurality of different times within multiple user selectable patient parameter acquisition time intervals comprising a time period;
  determining for a particular user selectable acquisition time interval a patient parameter data value closest in time to a substantially centre time point of said particular user selected acquisition time interval;
  excluding other patient parameter data values acquired within said particular user selectable acquisition time interval; and
  generating data representing an image showing a trend indicative display of said patient parameter including said determined patient parameter data value associated with said particular user selectable acquisition time interval and omitting said excluded data values.

15. A non-transitory storage medium according to claim 14, including computer readable instructions for implementing the activities of claim 14.

* * * * *